(12) United States Patent
Hooshyar et al.

(10) Patent No.: US 10,302,580 B2
(45) Date of Patent: May 28, 2019

(54) METHOD OF ANALYZING AN IRON MELT

(71) Applicant: VOLVO TRUCK CORPORATION, Göteborg (SE)

(72) Inventors: Hamed Hoseini Hooshyar, Göteborg (SE); Pål Schmidt, Göteborg (SE)

(73) Assignee: Volvo Truck Corporation, Göteborg (SE)

( * ) Notice: Subject to any disclaimer, the term of this patent is extended or adjusted under 35 U.S.C. 154(b) by 896 days.

(21) Appl. No.: 14/653,927

(22) PCT Filed: Dec. 21, 2012

(86) PCT No.: PCT/EP2012/005335
§ 371 (c)(1),
(2) Date: Jun. 19, 2015

(87) PCT Pub. No.: WO2014/094805
PCT Pub. Date: Jun. 26, 2014

(65) Prior Publication Data
US 2015/0316525 A1 Nov. 5, 2015

(51) Int. Cl.
*G01N 25/04* (2006.01)
*G01N 33/20* (2006.01)

(52) U.S. Cl.
CPC .......... *G01N 25/04* (2013.01); *G01N 33/206* (2013.01)

(58) Field of Classification Search
CPC .. G01K 7/16; G01K 7/01; G01K 7/10; G01K 7/22; G01K 11/32; G01K 13/00;
(Continued)

(56) References Cited

U.S. PATENT DOCUMENTS

| 5,328,502 A | * | 7/1994 | Backerud | ................. C21C 1/10 75/377 |
| 5,503,475 A | * | 4/1996 | Yamaguchi | .......... G01K 13/125 374/139 |
| 5,615,730 A | | 4/1997 | Hiraoka et al. | |
| 5,804,006 A | * | 9/1998 | Kanno | ................. G01N 33/206 75/380 |

(Continued)

FOREIGN PATENT DOCUMENTS

| CN | 1240025 A | 12/1999 |
| CN | 1336964 A | 2/2002 |

(Continued)

OTHER PUBLICATIONS

Chinese Official Action (dated May 9, 2016) for corresponding Chinese App. 20128077938.2.

*Primary Examiner* — Manish S Shah
(74) *Attorney, Agent, or Firm* — WRB-IP LLP

(57) ABSTRACT

A method of analyzing an iron melt for producing compacted graphite iron includes receiving thermal data from cooling of a cast melt including a predetermined amount of carbon, magnesium, balance iron and unavoidable impurities, plotting the temperature of the cast melt against time such that a plotted time-temperature curve is generated, comparing the generated plotted curve to at least one reference curve, the reference curve representing a corresponding thermal analysis of another melt, the resulting nodularity of which is known, for the purpose of predicting the nodularity of the cast melt on basis of the difference between the curves. The comparison on which the nodularity is predicted is performed along each of the curves for a time interval t1–t2 corresponding to a temperature interval T1–T2, where T1 is in the range of TEstart–TEmin where TEstart is the temperature of beginning formation of graphite in the melt and TEmin is a minimum temperature before start of eutectic recalescence in the melt, and T2 is in the range of Tsolidus–(Tsolidus–20° C.), and other time intervals in the curves are excluded from the comparison.

18 Claims, 6 Drawing Sheets

(58) Field of Classification Search
CPC ............... G01K 13/02; G01K 2205/04; G01K
2013/024; G01K 7/02; G01K 3/005;
G01K 3/10; G01K 7/42; B23K 31/02;
G01F 1/00; G01N 25/72; G01N 25/28;
G01N 25/32; G01N 33/225; H05K
7/20945; F24F 11/0012; F24F 2001/0052;
F24F 2011/0093; F24F 11/022; H02M
1/32; H02M 1/38; H02M 1/53806; H01C
7/008; H01C 1/14; H01C 17/00; H01R
4/023; H01R 4/029; H01R 43/28; G01R
31/2642; G01R 31/048; G01R 31/40;
G01J 5/004; G01J 5/00; G01J 5/003;
G01J 5/043; G01J 5/0821
See application file for complete search history.

(56) References Cited

U.S. PATENT DOCUMENTS

| 2004/0028548 | A1* | 2/2004 | Andersson | ............... C22C 33/08 |
| | | | | 420/12 |
| 2004/0103755 | A1* | 6/2004 | Beyerstedt | ................ C21C 1/06 |
| | | | | 75/566 |

FOREIGN PATENT DOCUMENTS

| CN | 1348099 A | 5/2002 |
| JP | H10206358 A | 8/1996 |
| JP | 2003053516 A | 2/2003 |
| JP | 2003121395 A | 9/2003 |

\* cited by examiner

METHOD OF ANALYZING AN IRON MELT

BACKGROUND AND SUMMARY

The present invention relates to a method of analyzing an iron melt for producing compacted graphite iron, comprising the steps of: receiving thermal data from cooling of a casted melt comprising a predetermined amount of carbon, magnesium, balance iron and unavoidable impurities, plotting the temperature of the cast melt against time such that a plotted time-temperature curve is generated, and comparing the generated plotted curve to at least one reference curve, said reference curve representing a corresponding thermal analysis of another melt, the resulting nodularity of which is known, for the purpose of predicting the nodularity of the cast melt on basis of the difference between said curves.

The present invention also relates to a method of producing compacted graphite iron, comprising the steps of: providing a melt comprising a predetermined amount of carbon, magnesium, balance iron and unavoidable impurities, casting at least a part of the melt in a mold, and performing a thermal analysis on the cast melt during cooling thereof in accordance with the analysis method of the invention.

The invention also relates to: a computer program comprising program code means for performing all the steps of the inventive analysis method when said program is run on a computer; a computer program product comprising program code means stored on a computer readable medium for performing all the steps of the analysis method of the invention when said program product is run on a computer, and; a computer system for implementing the analysis method of the invention comprising a processor operable to run a computer program according to the invention.

Cast irons are differentiated by the shape of the graphite particles. Grey cast iron is characterized by randomly oriented graphite flakes, while the graphite in ductile iron exists as individual spheres. The graphite particles in CGI are randomly oriented and elongated as in grey iron, but they are shorter, thicker and have rounded edges.

In comparison to either grey iron or ductile iron, the entangled compacted graphite clusters interlock themselves into the iron matrix to provide a strong adhesion. This graphite shape suppresses crack initiation and propagation and is the source of both the increased mechanical properties relative to grey iron and the improved thermal conductivity relative to ductile iron. These advantageous properties of CGI have made it a suitable material for cylinder blocks of internal combustion engines, in particular diesel engines. High titanium content CGI is also commonly used in exhaust manifold and power steering pump parts thanks to a very good thermal conductivity and high-temperature strength.

The graphite microstructure of Compacted Graphite Irons is expressed in terms of percent nodularity. For simultaneous optimization of mechanical properties, castability, machinability and thermal conductivity, the graphite should be controlled within 0-20% nodularity specification range (more than 80% of the graphite particles must be in the compacted/vermicular form) in all performance-critical sections of the casting. Flake graphite is not permitted. The nodularity percentage and the ferrite/pearlite matrix structure can be evaluated by so called chart comparison technique or by image analysis, both of which are standardized and well known to the person skilled in the art.

It is well-known in the present field of technology that the content of magnesium as an alloying element in the iron melt is of vital importance to the formation of nodules in the cast material and the resulting CGI microstructure. However, not only the Mg but also other alloying elements are involved in the process that leads to the generation of CGI. For example, graphite nodularity after magnesium treatment is affected by low initial sulfur level and this in turn may lead to nodular graphite formation at lower residual magnesium in the treated iron. Accordingly, increasing the sulfur addition, for the same magnesium addition, could be one possible way of promoting the formation of CGI for a given melt. However, it should be born in mind that magnesium is still regarded as the key element in order to obtain CGI, and fine calibration of the Mg content is a very efficient way of affecting the formation of CGI.

When the nodularity is to be predicted and controlled by means of the addition of magnesium, the amount of sulfur and oxygen plays an important role to the amount of magnesium that will be needed. Normally, the sulfur content in the melt is possible to control by a precise addition thereof. The content of oxygen is, on the other hand, not so easy to control or to monitor. Therefore, there will always be a certain degree of uncertainty of how much magnesium that will be required in order to obtain a specific nodularity.

In order to predict the nodularity for a specific melt prior art suggests a plurality of different methods. One such method is disclosed by Y. X. Li, Q. Wang; "Intelligent evaluation of melt iron quality by pattern recognition of thermal analysis cooling curves" J. Mat. Proc. Tech. 161 (2005) pp. 430-434. This method is based on the assumption that two melts with identical cooling curves, i.e. curves in which the temperature of the cast melt is plotted against time, and melt composition will also result in identical microstructures. The method presented by Li and Wang is a calculation of curve similarity in which a comparison of a plotted curve and at least one reference curve comprises measurement of temperature difference for predetermined times, and comparison of curve shape of said curves, and weighing together differences obtained by said comparison in order to present a difference value $\Omega$ on which the prediction of said nodularity is based. However, the method does not take into consideration that there may be variations in a) initial (pouring) temperature of the melt, b) the thermal cup filling ratio, and c) the carbon equivalent between the two castings that are compared to each other (the carbon equivalent of the melt being expressed as $CE=C+Si/4+P/2$ or, as an alternative, $CE=C+(Si+P)/3$, where C is mass % carbon, Si mass % sulfur and P is mass % phosphor). The present inventors have, however, realised that, due to said variations, also curves that, as analysed with the method of Li and Wang, have a rather different $\Omega$ may result in irons of very similar or almost identical nodularity.

It is desirable to present an alternative method of analyzing an iron melt by means of which an improved prediction of the nodularity of the cast melt compared to that of prior art is obtained, as well as an alternative method of producing compacted graphite iron with the aid of said analysis method.

According to a first aspect of the invention, in the initially defined method for analyzing an iron melt, said comparison on which the nodularity is predicted is performed along each of said curves for a time interval t1–t2 corresponding to a temperature interval T1–T2, where T1 is in the range of TEstan–TEmin, where TEstart is the temperature of beginning formation of graphite in the melt and TEmin is a minimum temperature before start of eutectic recalescence in the melt, and T2 is in the range of Tsolidus–(Tsolidus–20° C.), and that other time intervals in said curves are excluded from said comparison. It has been found that it is the given range of t1–t2 that gives a significant contribution to the analysis, and that further regions of the curves outside said range may, because of differences in the carbon equivalent between the analysed melt and the references melt, provide an important contribution to the calculated Ω value that, however, is less important to the nodularity than previously expected. By eliminating said further ranges from the analysis, the effect of different carbon equivalents is thus taken into consideration and differences in a calculated Ω that are due to such differences are thus excluded from the analysis.

According to a second aspect of the invention in the initially defined method for analyzing an iron melt, any of said curves is multiplied with a time factor such that the length of the curves expressed as t2 minus t1 becomes the same. Because of differences in the casting conditions, typically differences in the thermal cup filling ratio, the total time from the start of the casting to the end thereof, when the melt has solidified and reached a certain temperature, may vary between the analysed melt and the reference melt and thereby contribute to an incorrectly high Ω value that is not representative for the factual differences between the two melts. By means of the hereby suggested measure, the contribution to the Ω value caused by different casting conditions is thus eliminated or at least suppressed.

According to a preferred embodiment of said second aspect of the invention, the comparison on which the nodularity is predicted is performed along each of said curves for a time interval t1–t2 corresponding to a temperature interval T1–T2, where T1 is in the range of TEstart–TEmin, where TEstan is the temperature of beginning formation of graphite in the melt and TEmin is a minimum temperature before start of recalescence in the melt, and T2 is in the range of Tsolidus–(Tsolidus–20° C.), and that other time intervals in said curves are excluded from said comparison. Accordingly this is a combination of the first aspect and the second aspect. By the combination thereof, variations in the carbon equivalent as well as in the thermal cup filling ratio are compensated for in the analysis, and detrimental effects on a calculated Ω value caused by such variations are avoided.

According to one embodiment of the invention T2 is in the range of Tsolidus–(Tsolidus–10° C.), and according to a preferred embodiment T2 is Tsolidus. It has been found that the contribution to a (value from differences between different castings for the time range after that Tsolidus has been reached do not give any particular improvement of the analysis result but may rather have a negative impact thereon. Therefore, it is preferred not to base the analysis on parts of the plotted curves that reflect the time after that Tsolidus has been reached.

According to one embodiment, T1 is TEmin—The advantage of choosing this point as the starting point of the comparison interval is that it is reasonably easy to detect in the plotted curve and that, up to that point, possible differences between the plotted curve of the analysed melt and of any reference melt is of less importance to the prediction of the nodularity, as already described above.

According to yet another embodiment, T1 is TEstart—It should be mentioned that TEstart is in reality very close to TEmin as seen along the time axis in the plotted curve. Thus, the technical effect in terms of suppression of the effect of variations in carbon equivalent is not so different from that of having TEmin as a starting point. Likewise to TEmin, also TEstart has the advantage of being relatively easy to detect on a typical thermal analysis curve for a cast iron. TEstart is a defined by a local minimum in the first order derivative of the temperature, and by the second order derivative thereof being zero, i.e. defining a point of inflexion. By means of polynomial-adapted data, this inflexion point is relatively easy to detect.

According to one embodiment of the invention, any of said plotted curve and said reference curve is shifted along its time-axis such that it is equal for the two curves. In other words, shifting of at least one of the curves along the time axis is performed such that tr of the reference curve is located at the same position along the time axis as of the plotted (and analysed) curve. Thereby, regard is taken to the fact that there may be differences in initial (pouring) temperature of the analysed melt and the reference melt, and that the time when TEmin or TEstart occurs for the respective sample might differ and that, initially, t1 of curves are therefore displaced relative to each other along the time axis. Preferably, this step is to be taken after the establishment of the interval t1–t2 by which the curves of the analysed melt and the reference melt are adapted to each other in accordance with the teaching of the invention. Advantageously, this step is followed by the step in which any of said curves is multiplied with a time factor such that the length of the curves expressed as t2 minus t1 becomes the same.

According to one embodiment of the invention, said plotted curve is compared to a plurality of different reference curves for melts of different final nodularity, and the predicted nodularity is chosen to be the known nodularity of the reference curve that is defined as least different from the plotted curve. This technique is advantageous in those cases in which there is a large number of reference curves to compare with, such that there is a rather good chance of finding a curve that is very similar to the one of the analysed melt. The actual determination of the difference between the curves may be any one that is suitable for implementation in a computer program. It may, alternatively, be an ocular determination, preferably made by any experienced operator.

According to one embodiment, the comparison of the plotted curve and said at least one reference curve comprises measurement of temperature difference for predetermined times, and comparison of curve shape of said curves, and weighing together differences obtained by said comparison in order to present a difference value Ω on which the prediction of said nodularity is based.

According to one embodiment said melt consists of, in mass %:
C 3.0-4.0 preferably 3.55-3.80
Si 1.8-4.0 preferably 1.9-2.2
Cu 0-1.0 preferably 0.8-1.0
Mo 0-0.3
Mn 0.3-0.5
P 0-0.03
S 0.006-0.015
Sn 0.04-0.07
Cr 0-0.10
Tl 0-0.015
Mg 0.005-0.020 preferably 0.008-0.015
Ni 0-0.05
balance Fe and unavoidable impurities.
Melts with such a composition are advantageous for the purpose of producing a compacted graphite iron with nodularity and further mechanical properties that will be acceptable and advantageous for many applications.

Preferably, the carbon equivalent of the melt, expressed as CE=C+Si/4+P/2 where C is mass % carbon, Si mass % sulfur and P is mass % phosphor, is in the range of 4.0-4.4%.

Another aspect of the invention is also achieved by means of the initially defined method for producing a compacted graphite iron, which is characterized in that that the content of a nodularity-affecting agent in a remaining part of said melt, that has not been yet cast, is altered as a response to the predicted nodularity being outside a predetermined range, or that the content of a nodularity-affecting agent in a second melt, the characteristics of which corresponds to the characteristics of the cast melt as regards composition, casting temperature and carbon equivalent, is altered as a response to the predicted nodularity being outside a predetermined range. In other words, the analysis according to the present invention is taken advantage of in a production process, wherein the content of a nodularity-affecting agent in a melt is controlled on basis of the nodularity prediction for the melt on which the analysis is performed. The term "nodularity-affecting" could also be referred to as "vermicularity-affecting".

Preferably, the content of said nodularity-affecting agent in said remaining part of the melt or in said second melt is altered to such a level that a predicted nodularity of the melt, now comprising said altered content of the nodularity-affecting agent, is within said predetermined range. How much of the nodularity-affecting agent that is to be added to the melt may be decided on basis of prior data from further reference melts or by means of any suitable calculation method by means of which the desired amount is predicted. Possibly, or even preferably, a further test casting and thermal analysis in accordance with the teaching of the present invention is performed after addition of said nodularity-affecting agent in order to establish whether the requested nodularity within said predetermined range has been obtained. If needed, further adjustment of said nodularity-affecting agent is made, followed by yet a test casting and analysis, until a predicted nodularity within said range is obtained.

According to one embodiment, said nodularity-affecting agent is magnesium, Mg. Other possible agents the content of which could be altered as a response to the result of the nodularity prediction are cerium, calcium and/or titanium. Normally, the nodularity agent is added in order to increase the nodularity. However, if the nodularity is too high, a nodularity-affecting agent that suppresses the nodule generation or counteracts the nodularity-affecting effect of, for example, Mg could be added.

According to yet another embodiment, the amount of Mg in said melt is increased if the nodularity is below a predetermined threshold value.

The invention also relates to a computer program comprising program code means for performing one or more, preferably all, the steps of the inventive analysis method when said program is run on a computer.

The invention also relates to a computer program product comprising program code means stored on a computer readable medium for performing one or more, preferably all, the steps of the inventive analysis method when said program product is run on a computer.

Furthermore, the invention also relates to a computer system for implementing the analysis method of the invention, comprising a processor operable to run a computer program according to the invention.

Further features and advantages of the present invention will be presented in the following detailed description of an embodiment thereof.

BRIEF DESCRIPTION OF THE DRAWING

An embodiment of the present invention will now be described more in detail with reference to the annexed drawing, on which.

DETAILED DESCRIPTION

Figure 1:
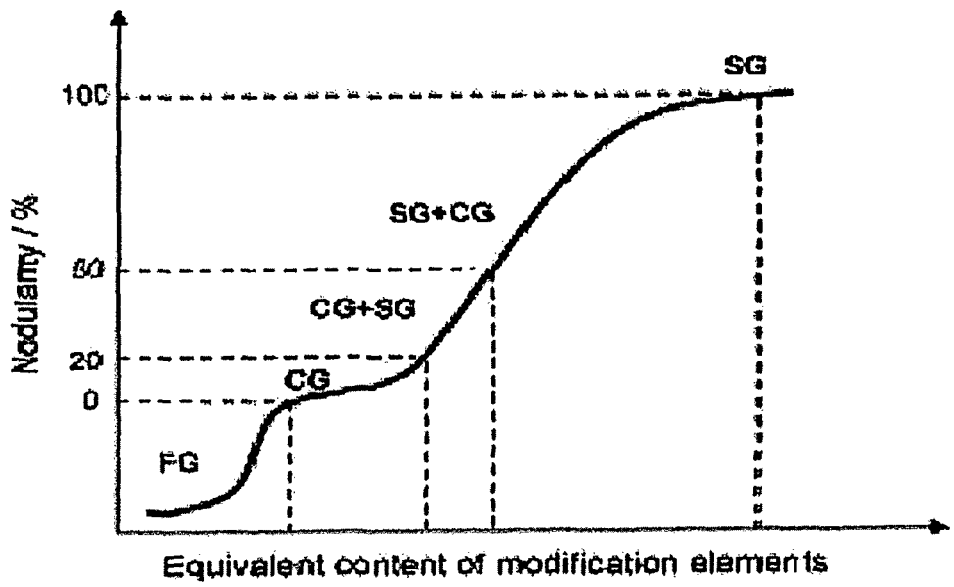
FIG. 1 is a schematic diagram presenting nodularity against content of nodularity-affecting agent, typically Mg.

FIG. 1 is a diagram showing the principles of how the content of a specific nodularity-affecting agent (named modification elements in FIG. 1), typically magnesium, affects the microstructure of a cast iron in which said agent forms an alloying element. FG stands for Flake Graphite, CG stands for Compacted Graphite, and SG stands for Spheroidal Graphite. The graphite microstructure of Compacted Graphite Irons is expressed in terms of percent nodularity. According to a preferred embodiment of the present invention, for simultaneous optimization of mechanical properties, castability, machinability and thermal conductivity, the graphite should be controlled within 0-30% nodularity specification range, preferably within the 0-20% nodularity specification range (more than 80% of the graphite particles should be in the compacted/vermicular form), in all performance-critical sections of a casting. According to the present invention flake graphite is not permitted. For the particular example of an iron in which magnesium is used as the sole or at least predominant agent for affecting the nodularity, the effective range of magnesium within which 0-20% nodularity is obtained is rather narrow, typically in the range of 0.008-0.014 mass % Mg.

According to the general concept of the present invention, there is suggested a method of analyzing an iron melt for producing compacted graphite iron, comprising the steps of: receiving thermal data from cooling of a cast melt comprising a predetermined amount of carbon, magnesium, balance iron and unavoidable impurities; plotting the temperature of the cast melt against time such that a plotted time-temperature curve is generated, and; comparing the generated plotted curve to at least one reference curve, said reference curve representing a corresponding thermal analysis of another melt, the resulting nodularity of which is known, for the purpose of predicting the nodularity of the cast melt on basis of the difference between said curves. Preferably, the method of analyzing is applied in a method of producing compacted graphite iron, comprising the steps of: providing a melt comprising a predetermined amount of carbon, magnesium, balance iron and unavoidable impurities; casting at least a part of the melt in a mold, and; performing a thermal analysis on the cast melt during cooling thereof in accordance with the invention, wherein the content of a nodularity-affecting agent in a remaining part of said melt, that has not been yet cast, is altered as a response to the predicted nodularity being outside a predetermined range, or wherein the content of a nodularity-affecting agent in a second melt, the characteristics of which corresponds to the characteristics of the cast melt as regards composition, casting temperature and carbon equivalent, is altered as a response to the predicted nodularity being outside a predetermined range.

Figure 2:
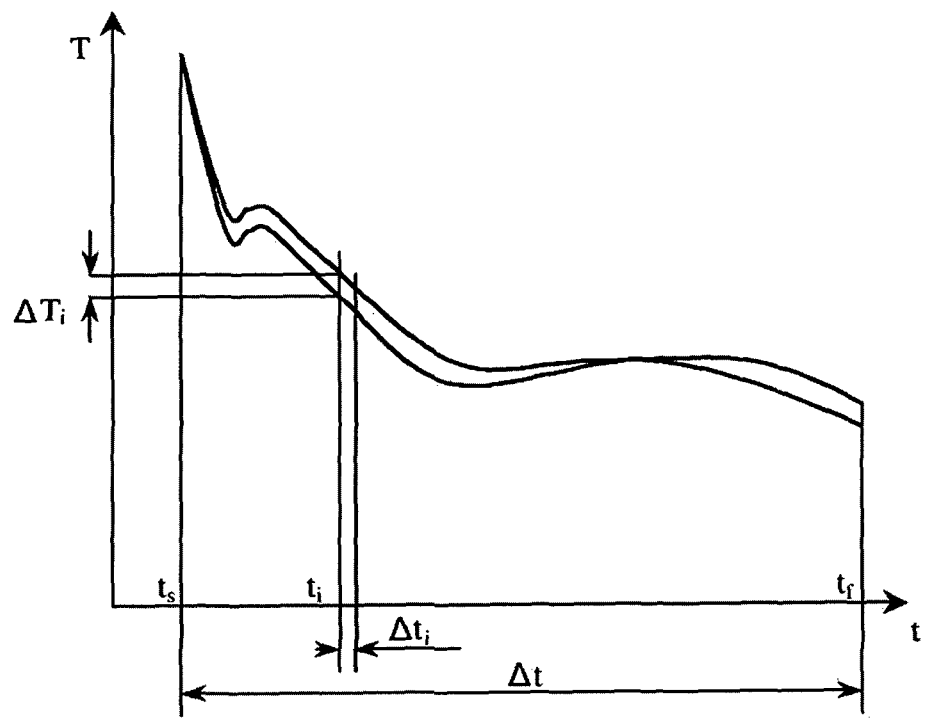
FIG. 2 is a diagram showing the principle for shape recognition of cooling curves in accordance with the teaching of prior art.

The analysis method of the invention is based on the assumption that two melts with identical cooling curves, i.e. curves in which the temperature of the cast melt is plotted against time, and melt composition will also result in identical microstructures. FIG. 2 is a representation of a calculation of curve similarity in which a comparison of a plotted curve and at least one reference curve comprises measurement of temperature difference for predetermined times (increments), and comparison of the curve shape of said curves, and weighing together differences obtained by said comparison in order to present a difference value $\Omega$ on which the prediction of said nodularity is based. According to one embodiment of the present invention, these principles are applied for the calculation of a difference value $\Omega$ for the prediction of the nodularity of a test melt. However, as will be disclosed later, the present invention differs from prior art in that it suggests specific adjustments of the curves on which said method of analyzing is performed.

In FIG. 2, ts is the time of start of the casting, tf represents the final of the casting, for example when a given time since start of casting has passed and the temperatures of the respective curve indicates that both castings have reached the solidus temperature and are thus in a fully solidified state. T is temperature.

From the curves compared in FIG. 2, a total temperature difference S between the two curves is calculated as follows:

$$S = \left[ \frac{\sum (\Delta Ti - \overline{\Delta T})^2}{n-1} \right]^{1/2}$$

wherein $\Delta Ti = Ti - T'i$ and $\overline{\Delta T} = \left( \sum \Delta Ti \right) / n$ and wherein:
i is the time step normally an integer from 1 to n
n is the total number of steps
$T_i$ is the temperature of melt of analysed curve at time $t_i$
$T'i$ is the temperature of melt of reference curve at time $t_i$.

Finally, a difference value $\Omega$ is calculated in accordance with the following formula, referred to as formula I in the following.

$$\left[ \frac{\sum \Delta Ti}{n} \right] + S$$

Figure 6:
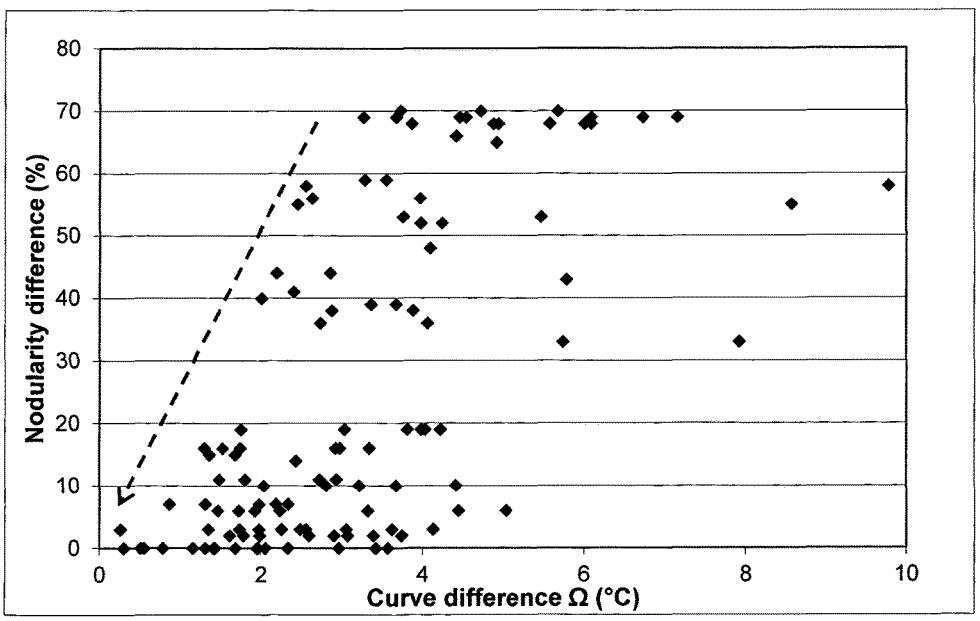
FIG. 6 is a diagram showing results of analyses for different melts, for which nodularity is plotted against calculated $\Omega$ with regard to a reference melt.

The obtained difference value $\Omega$ is used for predicting the nodularity of the test melt. Preferably, a plurality of reference curves, representing melts with resulting nodularity within as well as outside a requested predetermined range, are used for comparison with the test melt. When $\Omega$ gets close to zero with regard to any of said reference curves, the nodularity of the test melt is expected to be approximately the nodularity of that reference melt. This can be seen in FIG. 6, showing results of analyses for different melts, for which nodularity is plotted against calculated $\Omega$ with regard to a reference melt.

Figure 3:
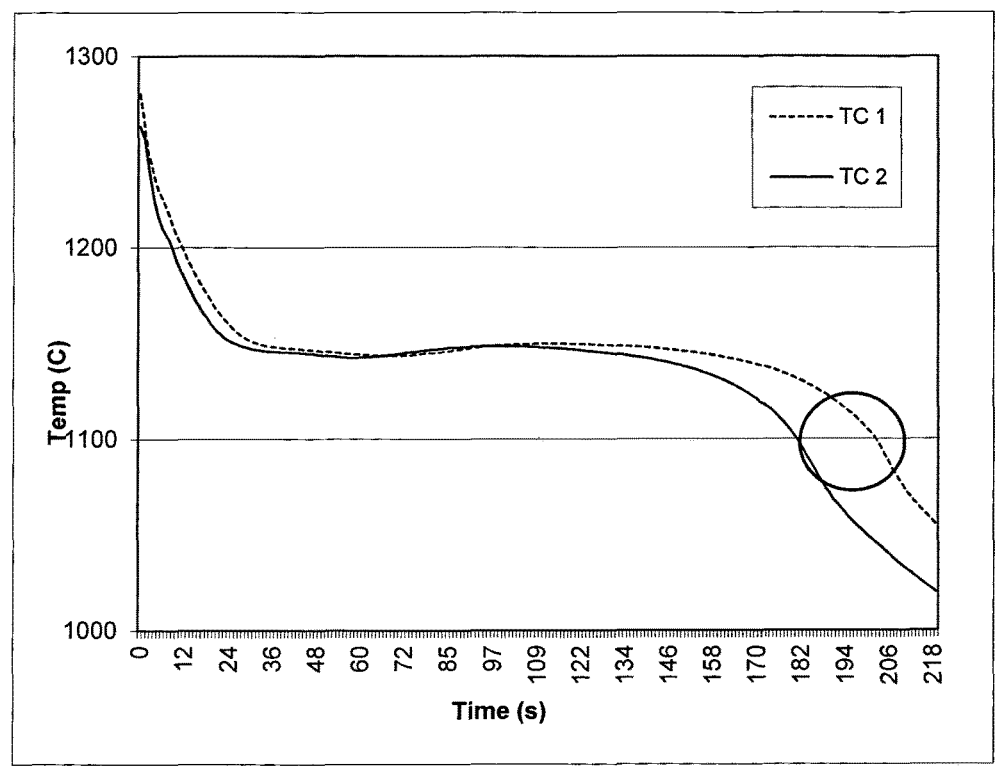
FIG. 3 shows two cooling curves with different initial temperatures leading to different total solidification times.
Figure 4:
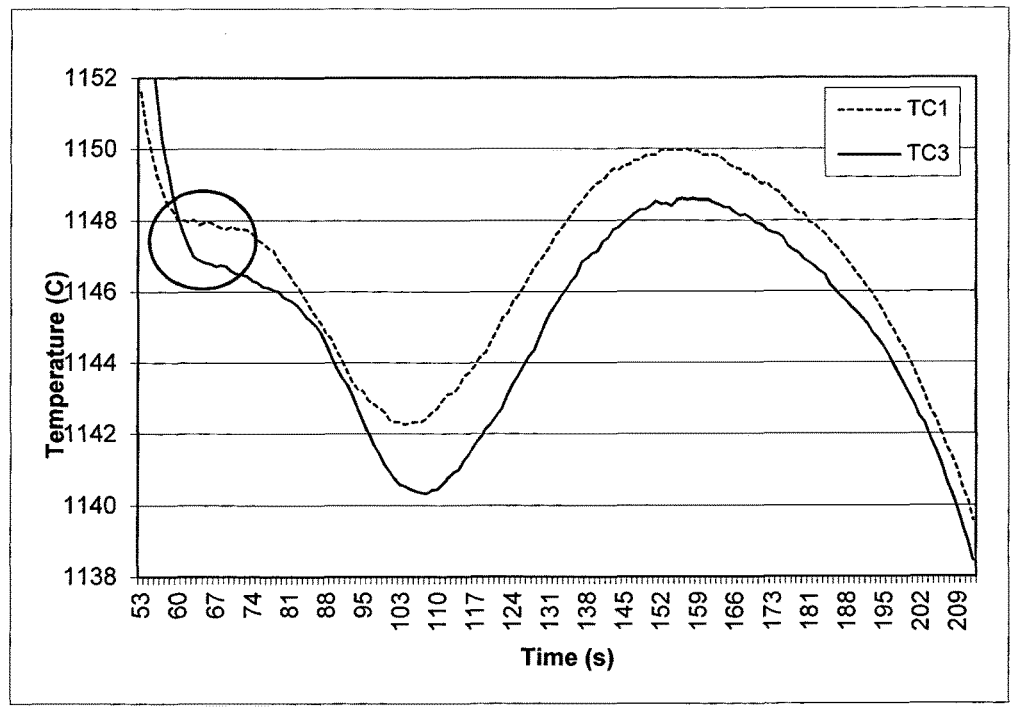
FIG. 4 shows two melts with different carbon equivalents leading to different liquidus temperatures (TL).

However, according to prior art, the above-described method does not take into consideration that there may be variations in a) initial (pouring) temperature of the melt, b) the thermal cup filling ratio, and c) the carbon equivalent between the two castings that are compared to each other. FIG. 3 is a representation of two cooling curves, referred to as TC1 and TC2, with different initial temperatures leading to different total solidification times, and FIG. 4 is a representation of two melts, the cooling curves of which are referred to as TC1 and TC3, with different carbon equivalents leading to different liquidus temperatures (TL). If the curves are not adjusted with regard to these differences, the difference value $\Omega$ will become unreasonably high and thus not representative for the actual nodularity of the test melt. This explains the fact that in FIG. 6, which represents nodularity predictions in accordance with prior art, there is a plurality of examples in which the difference in nodularity is actually very small though the difference value $\Omega$ is rather high. The inventors have realized that there are parts of the curves that are less relevant for the actual difference in nodularity between a reference melt and a test melt.

Figure 5:
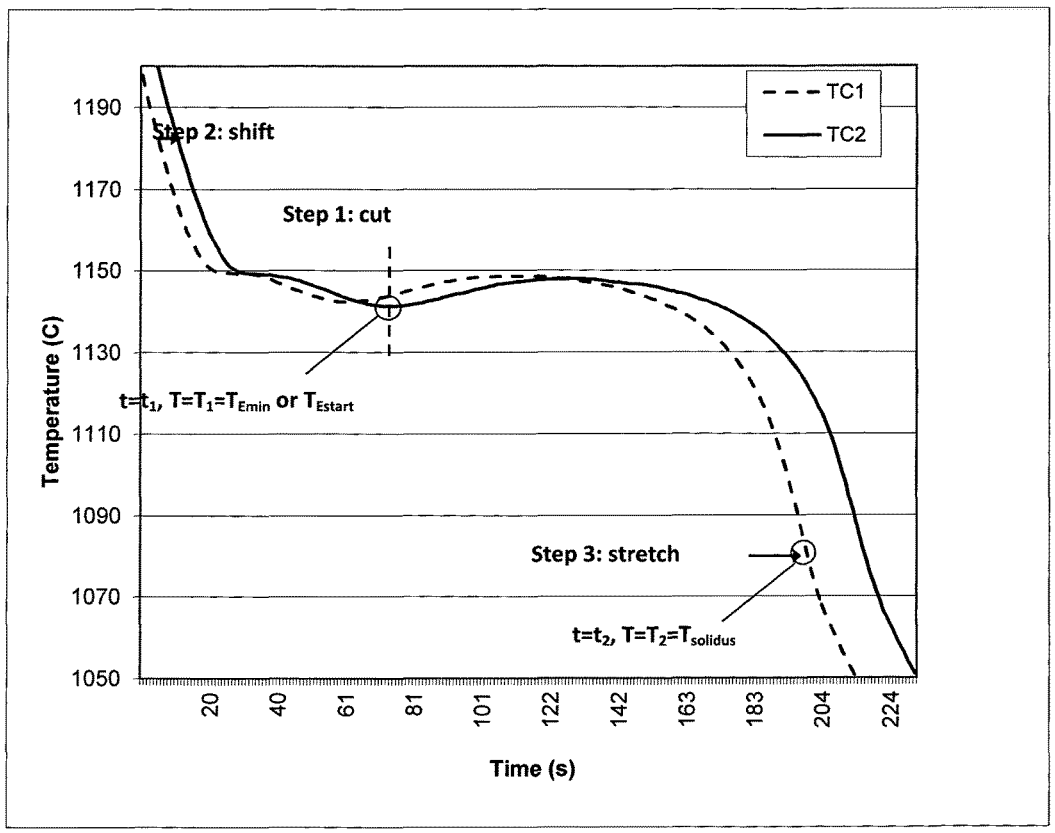
FIG. 5 is a diagram showing basic principles of the analyzing method of the present invention.

Therefore, according to a preferred embodiment of the present invention, represented by way of example in FIG. 5, it is suggested that the following measures are taken before the calculation of the difference value $\Omega$ is performed in accordance with the above principle:

1. The curves are cut at t1 which, according to a preferred embodiment is equal to TEmin, where TEmin is the minimum temperature before start of recalescence in the melt. TEmin is relatively easy to detect for a person skilled in the art. Alternatively, t1 is equal to TEstart, which is the temperature of beginning formation of graphite in the melt. Also TEstart is relatively easy to detect for a person skilled in the art. The time interval ranging from t0 to is thus excluded from the subsequent comparison of the two curves by means of the above-defined method of calculating the difference value $\Omega$. Further to cutting the curves at t1 the latter are also cut at t2, which corresponds to the time at which the respective curve reaches a temperature T2 which is approximately Tsolidus. The time interval ranging from t2 to the end of the thermal analysis, which might be room temperature depending on how long the plotting of temperature has been permitted to proceed, is thus excluded from the subsequent comparison of the two curves by means of the above-defined method of calculating the difference value $\Omega$.

2. Shift one of the curves along the time axis such that the temperature at t1 is approximately the same (is located at the same place along the time axis of the curves) for the two curves that are to be compared. Thereby, compensation is made for possible different initial temperatures presented by the original, non-adjusted curves.

3. Stretch any of the remaining curves (that now extend from t1 to t2) such that the length of the curves expressed as t2 minus t1 becomes the same. Stretching is done by multiplying any of the curves with a factor such that said length becomes the same. Thereby, differences in casting conditions, in particular the thermal cup filling ratio, is compensated for.

After that the above adjustments of the curves have been made, the curves are compared in accordance with the principle described above with reference to FIG. 2. In this way, the plotted curve is compared to a plurality of different reference curves for melts of different (and known) final nodularity, and the predicted nodularity is chosen to be the known nodularity of the reference curve that is defined as least different from the plotted curve, i.e. the curve for which the difference value Ω is the lowest.

According to an embodiment of the invention, the above analysis and prediction of the nodularity for a specific melt forms part of a method for producing a compacted graphite iron. According to one embodiment of the invention said method comprises the steps of providing a melt comprising a predetermined amount of carbon, magnesium, balance iron and unavoidable impurities, casting at least a part of the melt in a mold, and performing a thermal analysis on the cast melt during cooling thereof and predicting the nodularity thereof in accordance with the above-described teaching. Thereafter, the content of a nodularity-affecting agent in a remaining part of said melt, which has not been yet cast, is altered as a response to the predicted nodularity being outside a predetermined range, said range preferably being 0-30% nodularity, and even more preferably 0-20% nodularity, in accordance with the previous teaching (wherein the nodularity preferably is estimated in accordance with ISO 16112: 2006, appendix B). Alternatively, the content of a nodularity-affecting agent in a second melt, the characteristics of which corresponds to the characteristics of the cast melt as regards composition, casting temperature and carbon equivalent, is altered as a response to the predicted nodularity being outside said predetermined range (0-30% nodularity or 0-20% nodularity). Preferably, the nodularity-affecting agent the content of which is altered is magnesium. If insufficient nodularity, i.e. insufficient amount of vermicular graphite, is predicted, magnesium is added to the melt in order to obtain sufficient nodularity. A further test casting and analyzing thereof in accordance with the above-defined method according to the invention may be performed in order to make sure that the melt with its adjusted content of the nodularity-affecting agent will have a predicted nodularity within said predetermined range. The degree of increase of the nodularity-affecting agent is made on basis of prior knowledge regarding how much effect on nodularity a certain addition thereof will have.

According to a preferred embodiment of the invention, said melt consists of, in mass %:
C 3.0-4.0 preferably 3.55-3.80
Si 1.8-4.0 preferably 1.9-2.2
Cu 0-1.0 preferably 0.8-1.0
Mo 0-0.3
Mn 0.3-0.5
P 0-0.03
S 0.006-0.015
Sn 0.04-0.07
Cr 0-0.10
Tl 0-0.015
Mg 0.005-0.020 preferably 0.008-0.015
Ni 0-0.05
balance Fe and unavoidable impurities. The carbon equivalent of the melt, expressed as CE=C+Si/4+P/2, where C is mass % carbon, Si mass % sulfur and P is mass % phosphor, is in the range of 4.0-4.4%. Preferably, but not necessarily, also the melt on basis of which a reference curve is presented and with which the melt is compared in accordance with the teaching of the invention has a composition within the above-defined ranges.

EXAMPLES

Melts with the compositions according to table 1 (in mass %) were prepared in an induction furnace of medium frequency type with a melting capacity of 4 ton. The melts were inoculated with 0.1% Inobar and 0.02% RE (rare earth). The composition of the respective melt was measured by means of a spectrometer. Cekv is the carbon equivalent of the respective melt, expressed as CE=% C+% Si/4+% P/2.

TABLE 1

| Trial No. | C | Si | Mn | P | S | Cr | Ni | Mo | Cu | Sn | Ti | Mg | Cekv |
|---|---|---|---|---|---|---|---|---|---|---|---|---|---|
| 1 | 3.67 | 2.20 | 0.38 | 0.005 | 0.009 | 0.03 | 0.02 | 0.01 | 0.96 | 0.059 | 0.02 | 0.009 | 4.22 |
| 2 | 3.60 | 2.28 | 0.36 | 0.006 | 0.010 | 0.03 | 0.02 | 0.01 | 0.91 | 0.056 | 0.022 | 0.010 | 4.37 |
| 3 | 3.61 | 2.22 | 0.36 | 0.005 | 0.008 | 0.03 | 0.02 | 0.01 | 0.92 | 0.061 | 0.022 | 0.008 | 4.17 |
| 4 | 3.72 | 2.22 | 0.40 | 0.005 | 0.011 | 0.03 | 0.02 | 0.01 | 0.96 | 0.059 | 0.02 | 0.010 | 4.27 |
| 5 | 3.69 | 2.25 | 0.35 | 0.005 | 0.011 | 0.03 | 0.02 | 0.01 | 0.94 | 0.062 | 0.02 | 0.009 | 4.15 |
| 6 | 3.62 | 2.23 | 0.38 | 0.006 | 0.010 | 0.04 | 0.02 | 0.01 | 0.94 | 0.059 | 0.02 | 0.009 | 4.18 |
| 7 | 3.69 | 2.23 | 0.37 | 0.006 | 0.009 | 0.03 | 0.02 | 0.01 | 0.96 | 0.061 | 0.02 | 0.012 | 4.25 |
| 8 | 3.65 | 2.28 | 0.38 | 0.006 | 0.010 | 0.04 | 0.02 | 0.01 | 0.93 | 0.060 | 0.023 | 0.012 | 4.21 |
| 9 | 3.68 | 2.26 | 0.38 | 0.006 | 0.010 | 0.04 | 0.02 | 0.01 | 0.93 | 0.060 | 0.022 | 0.012 | 4.21 |
| 11 | 3.71 | 2.02 | 0.38 | 0.007 | 0.011 | 0.04 | 0.02 | 0.01 | 0.89 | 0.047 | 0.014 | 0.009 | 4.21 |
| 12 | 3.70 | 2.02 | 0.41 | 0.008 | 0.011 | 0.04 | 0.02 | 0.01 | 0.88 | 0.046 | 0.015 | 0.009 | 4.21 |
| 13 | 3.64 | 2.04 | 0.42 | 0.007 | 0.011 | 0.04 | 0.02 | 0.01 | 0.87 | 0.046 | 0.015 | 0.008 | 4.16 |
| 14 | 3.67 | 1.98 | 0.38 | 0.007 | 0.009 | 0.04 | 0.02 | 0.01 | 0.88 | 0.048 | 0.014 | 0.007 | 4.16 |
| 15 | 3.69 | 2.05 | 0.41 | 0.008 | 0.010 | 0.04 | 0.02 | 0.01 | 0.88 | 0.048 | 0.015 | 0.010 | 4.20 |
| 16 | 3.67 | 2.04 | 0.40 | 0.008 | 0.010 | 0.04 | 0.02 | 0.01 | 0.88 | 0.048 | 0.015 | 0.009 | 4.15 |
| 21 | 3.74 | 2.10 | 0.36 | 0.005 | 0.008 | 0.03 | 0.03 | 0.01 | 0.87 | 0.043 | 0.009 | 0.012 | 4.26 |
| 22 | 3.66 | 2.08 | 0.36 | 0.005 | 0.008 | 0.03 | 0.03 | 0.01 | 0.87 | 0.041 | 0.009 | 0.010 | 4.18 |
| 23 | 3.76 | 1.93 | 0.33 | 0.005 | 0.009 | 0.03 | 0.03 | 0.01 | 0.86 | 0.036 | 0.008 | 0.004 | 4.24 |
| 24 | 3.70 | 1.97 | 0.36 | 0.005 | 0.009 | 0.03 | 0.03 | 0.01 | 0.87 | 0.041 | 0.009 | 0.004 | 4.19 |
| 25 | 3.73 | 2.10 | 0.36 | 0.02 | 0.010 | 0.05 | 0.02 | 0.01 | 0.82 | 0.041 | 0.010 | 0.015 | 4.25 |
| 26 | 3.75 | 2.13 | 0.36 | 0.005 | 0.010 | 0.03 | 0.03 | 0.01 | 0.86 | 0.040 | 0.009 | 0.014 | 4.28 |
| 31 | 3.76 | 2.24 | 0.42 | 0.005 | 0.011 | 0.03 | 0.03 | 0.01 | 0.87 | 0.050 | 0.010 | 0.021 | 4.31 |
| 33 | 3.72 | 2.02 | 0.39 | 0.005 | 0.011 | 0.03 | 0.03 | 0.01 | 0.88 | 0.051 | 0.008 | 0.005 | 4.22 |
| 34 | 3.69 | 2.03 | 0.38 | 0.005 | 0.011 | 0.03 | 0.03 | 0.01 | 0.86 | 0.049 | 0.006 | 0.005 | 4.20 |
| 35 | 3.76 | 2.04 | 0.38 | 0.005 | 0.010 | 0.03 | 0.03 | 0.01 | 0.89 | 0.051 | 0.008 | 0.008 | 4.27 |
| 41 | 3.72 | 2.04 | 0.38 | 0.005 | 0.009 | 0.03 | 0.03 | 0.01 | 0.88 | 0.073 | 0.010 | 0.008 | 4.23 |

Figure 7:
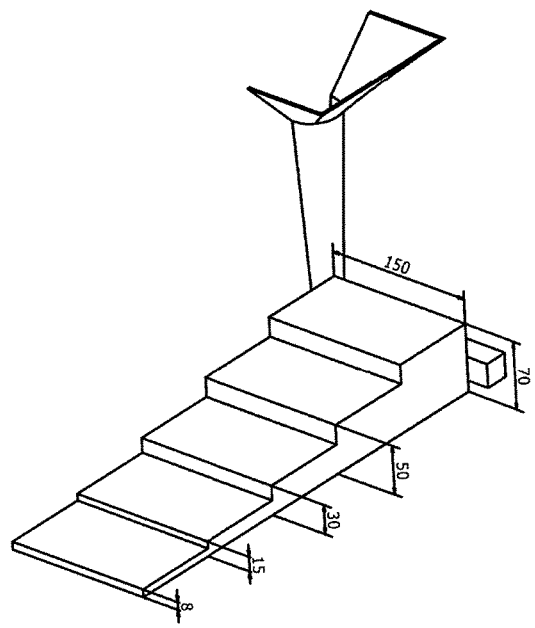
FIG. 7 is a schematic representation of the shape of test samples of molded iron.

Samples from the trial melts presented in table 1 were produced by casting the respective melt in a mold with a mold cavity that resulted in samples with staircase-like geometry, as presented in FIG. 7, with a thickness in the range of 8-70 mm (from thinnest step to thickest step).

During cooling of the cast melts, the temperature thereof versus time was measured by means of thermocouples type K (QuiK-Cup (manufacturer Heraeus Electro-Nite)) and plotted. The sampling rate was 1 Hz, and the obtained plots were smoothened by means of polynomial fitting.

The nodularity of each sample was estimated in accordance with ISO 16112:2006, appendix B (standard method for estimation of nodularity).

Samples were compared to each other by comparison of the resulting time-temperature plots thereof and calculation of the Ω value in accordance with the equations presented above, and in accordance with the principles of the present invention, i.e. cutting, shifting and stretching of one of two compared curves in accordance with the above-mentioned steps 1, 2 and 3 shown in FIG. 5. Cutting was done at TEmin as well as at TEstart for the purpose of comparing the resulting difference thereof on the calculated Ω value. Comparison is also done with a sample without performance of any of said steps.

Figure 8:
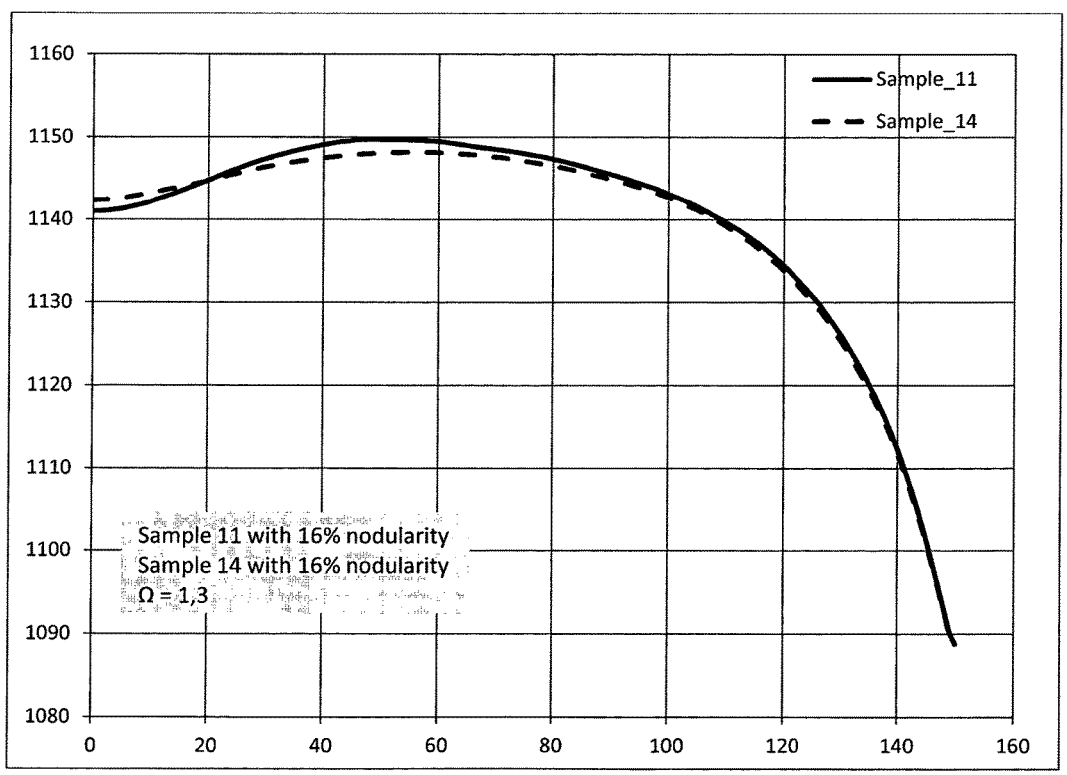
FIG. 8 is a diagram showing comparison of two curves in accordance with one embodiment of the present invention.

FIG. 8 is a representation of a comparison of samples 11 and 14 (both with a nodularity of 16%) by which cutting, shifting and stretching was performed on the curves in accordance with the principles of the invention. Cutting was done at TEmin and Tsolidus. Ω was calculated by means of formula I mentioned earlier. The resulting Ω value was as low as 1.3, thus indicating that the difference in nodularity is very small.

Figure 9:
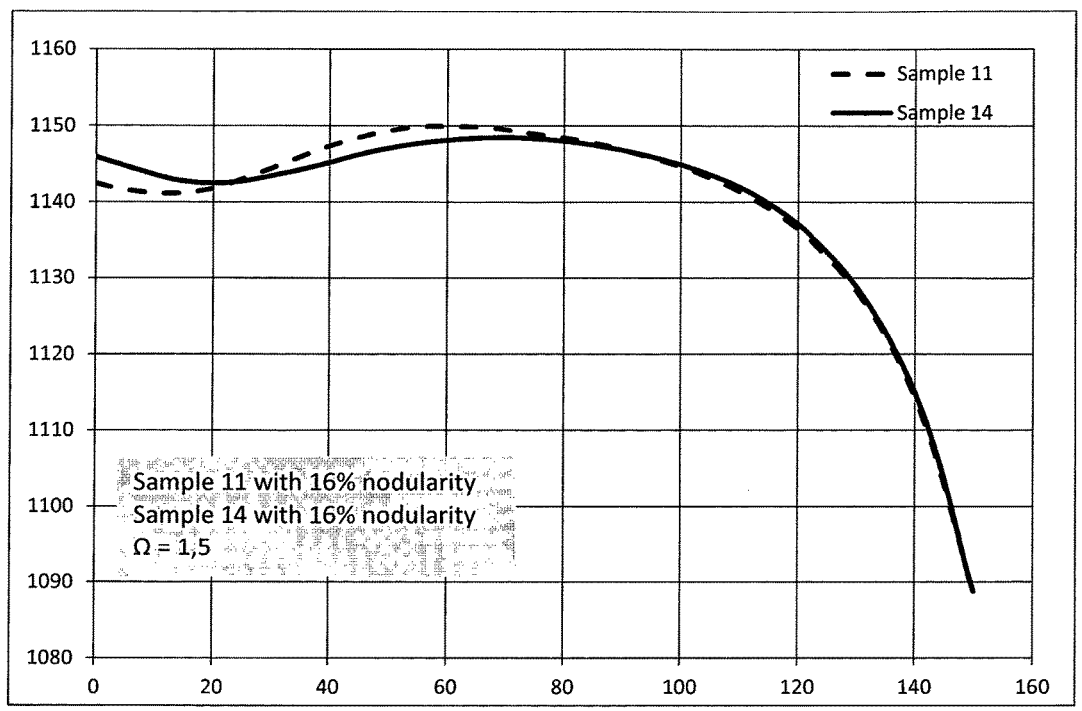
FIG. 9 is another diagram showing comparison of two curves in accordance with another embodiment of the present invention.

FIG. 9 is a representation of a comparison of samples 11 and 14 which differs from the one presented in FIG. 8 in that T1 is TEstart. The resulting Ω value is 1.5. Thus, the Ω value is still relatively low, indicating a similar nodularity for the compared samples, but not as low as for the case represented by FIG. 8. As can be assumed, an increase of the range of comparison, which is obtained when T1 being TEstart instead of TEmin results in a higher Ω value. However, the difference is relatively small, indicating that either of TEstart or TEmin may be used as T1.

Figure 10:
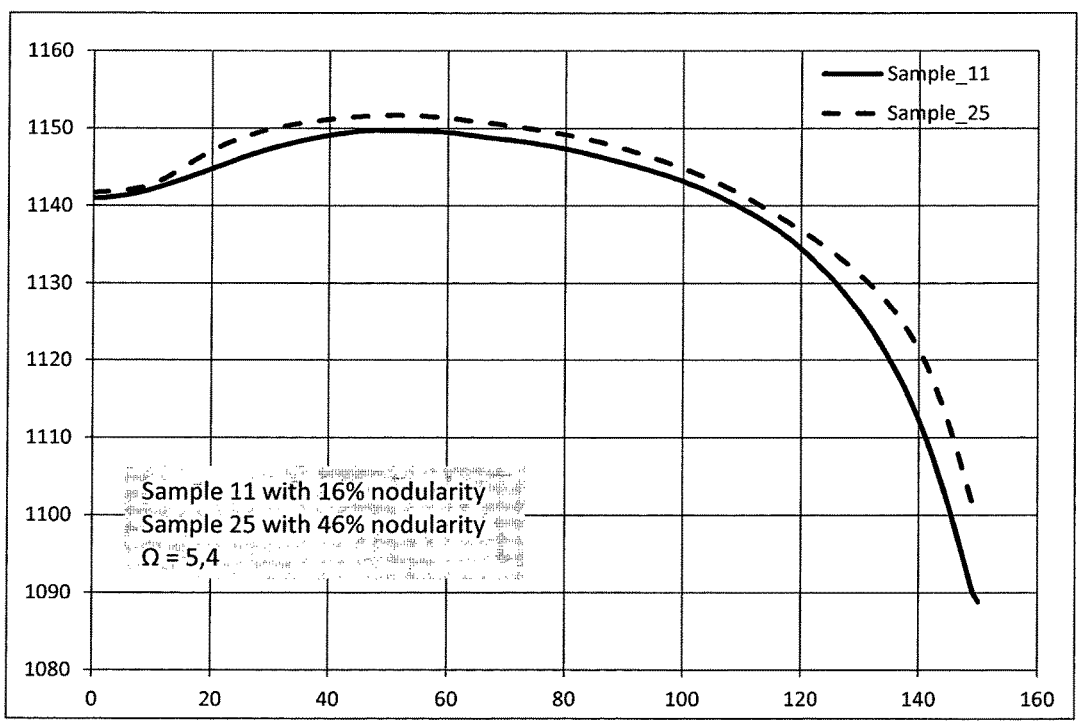
FIG. 10 is a diagram showing comparison of two curves.

FIG. 10 is a representation of a comparison of samples 11, having 16% nodularity, and 25, having 46% nodularity. The plots have been manipulated by cutting, shifting and stretching in accordance with the teaching of the invention, wherein T1 is TEmin and T2 is Tsolidus. The resulting Ω value is as high as 5.6, which is to be compared to the corresponding Ω value of 1.3 obtained for the comparison of samples 11 and 14. Thus, though the plotted curves have been manipulated in accordance with the teaching of the invention, in particular having been cut to the restricted range subjected to comparison, it is obvious that the manipulated curves are still effective for the purpose of identifying a difference in nodularity between different samples.

Figure 11:
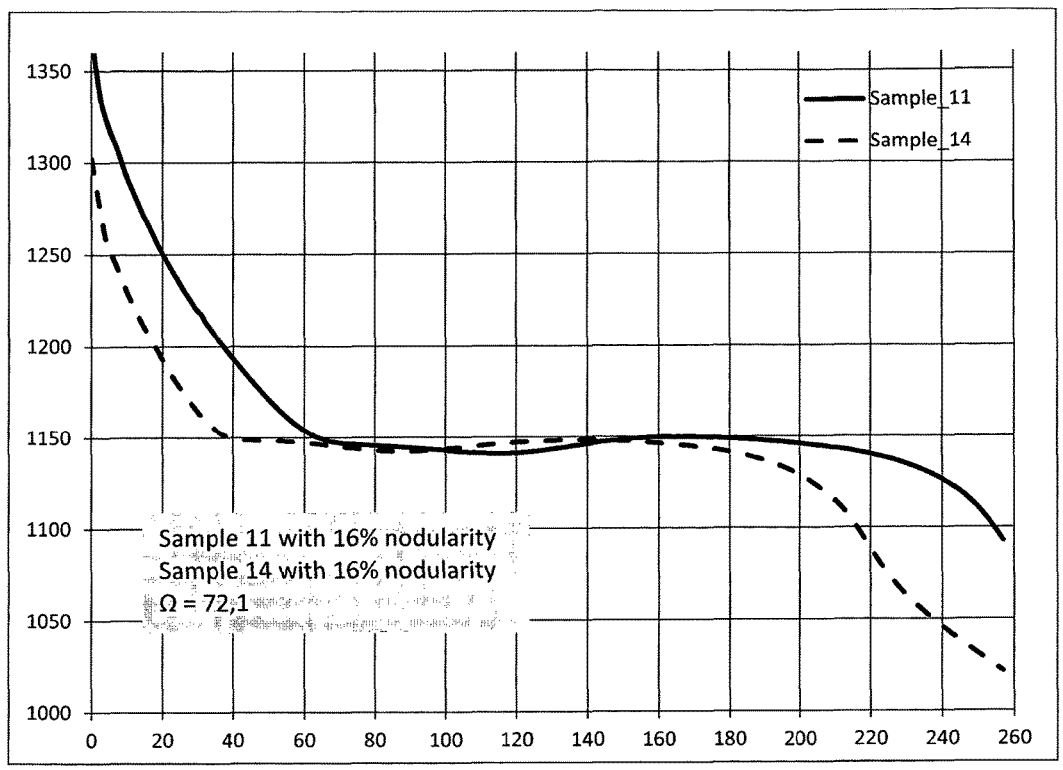
FIG. 11 is a diagram showing comparison of two curves without essential steps of the invention having been applied.

FIG. 11 is a representation of comparison of samples 11 and 14, both having a nodularity of 16%. The comparison differs from the one presented in FIG. 8 in that none of the curve manipulation steps of the present invention has been applied. The resulting Ω value is as high as 72.1. It is thus obvious that, in absence of steps 1, 2 and 3 as suggested by the present invention, a very high Ω value may be obtained also for samples that in fact have the same nodularity.

Sample 11 was compared to a number of the further samples presented in table 1 above. Steps 1, 2 and 3 of the present invention were applied and the Ω value for sample 11 was calculated in accordance with formula I previously presented. The results are presented in table 2.

TABLE 2

| Sample No. | Ω | Nod (QuiK-Cup) |
|---|---|---|
| 11 | 0.00 | 16 |
| 14 | 1.34 | 16 |
| 15 | 1.42 | 13 |
| 16 | 1.52 | 12 |
| 21 | 2.13 | 32 |
| 26 | 2.40 | 46 |
| 13 | 2.56 | 10 |
| 22 | 2.88 | 28 |
| 12 | 3.97 | 18 |
| 25 | 5.42 | 46 |
| 23 | 17.67 | 0 |
| 24 | 22.64 | 0 |

From table 2 it can be concluded that the present invention results in low Ω values when sample 11 is compared to samples with the same nodularity as sample. 11 or with nodularity close to the nodularity of sample 11, while higher Ω values were obtained when comparison was made with samples with significantly different nodularity than the one of sample 11. Accordingly, the present invention enables a rather precise estimation of the nodularity, and results in an estimation which is not misleading due to the factor played by the parts of the compared curves that have now been eliminated by cut off in accordance with the teaching of the present invention, as could be the case with corresponding estimation in accordance with prior art. Nonetheless, the present invention, though using a reduced part of the cooling data compared to prior art, results in the detection of differences in nodularity between compared samples.

It should be understood that the above examples are only presented by way of example and that the scope of protection claimed is not limited thereto, but instead limited by the scope of protection defined in the enclosed claims, supported by the description and the annexed drawing.

The invention claimed is:
1. A method of analyzing an iron melt for producing compacted graphite iron, comprising the steps of
   receiving thermal data from cooling of a cast melt comprising a predetermined amount of carbon, magnesium, balance iron and unavoidable impurities,
   plotting a temperature of the cast melt against time such that a plotted time-temperature curve is generated,
   predicting a nodularity of the cast melt by comparing the generated plotted curve to at least one reference curve, the reference curve representing a corresponding thermal analysis of another melt, a resulting nodularity of which is known, based on a difference between the curves,
   wherein the comparison on which the nodularity is predicted is performed along each of the curves for a time interval t1–t2 corresponding to a temperature interval T1–T2, where T1 is in the range of TEstart–TEmin, where TEstart is the temperature of beginning formation of graphite in the melt and TEmin is a minimum temperature before start of eutectic recalescence in the melt, and T2 is in the range of Tsolidus–(Tsolidus–20° C.), and other time intervals in the curves are excluded from the comparison.
2. A method according to claim 1, wherein T2 is in the range of Tsolidus–(Tsolidus–10° C.).
3. A method according to claim 1, wherein T2 is Tsolidus.
4. A method according to claim 1, wherein T1 is TEmin.
5. A method according to claim 1, wherein T1 is TEstart.

6. A method according to claim 1, wherein any of the plotted curve and the reference curve is shifted along its time-axis such that t1 is equal for the two curves.

7. A method according to claim 1, wherein the plotted curve is compared to a plurality of different reference curves for melts of different final nodularity, and that the predicted nodularity is chosen to be the known nodularity of the reference curve that is defined as least different from the plotted curve.

8. A method according to claim 1, wherein the comparison of the plotted curve and the at least one reference curve comprises measurement of temperature difference for predetermined times, and comparison of curve shape of the curves, and weighing together differences obtained by the comparison in order to present a difference value $\Omega$ on which the prediction of the nodularity is based.

9. A method according to claim 1, wherein the melt consists of, in mass %:
C 3.0-4.0
Si 1.8-4.0
Cu 0-1.0
Mo—0-0.3
Mn 0.3-0.5
P 0-0.03
S 0.006-0.015
Sn 0.04-0.07
Cr 0-0.10
Ti 0-0.015
Mg 0.005-0.020
Ni 0-0.05
balance Fe and unavoidable impurities.

10. A method according to claim 1, wherein the carbon equivalent of the melt, expressed as CE=C+Si/4+P/2 where C is mass % carbon, Si mass % sulfur and P is mass % phosphor, is in the range of 4.0-4.4%.

11. A method of producing compacted graphite iron, comprising
providing a melt comprising a predetermined amount of carbon, magnesium, balance iron and unavoidable impurities,
casting at least a part of the melt in a mold, and
performing a thermal analysis on the cast melt during cooling thereof in accordance with claim 1, wherein
a content of a nodularity-affecting agent in a remaining part of the melt, that has not been yet cast, is altered as a response to the predicted nodularity being outside a predetermined range, or
a content of a nodularity-affecting agent in a second melt, characteristics of which corresponds to the characteristics of the cast melt as regards composition, casting temperature and carbon equivalent, is altered as a response to the predicted nodularity being outside a predetermined range.

12. A method according to claim 11, wherein the content of the nodularity-affecting agent in the remaining part of the melt or in the second melt is altered-to such a level that a predicted nodularity based on the altered content of the nodularity-affecting agent is within the predetermined range.

13. A method according to claim 11, wherein the nodularity-affecting agent is magnesium, Mg.

14. A method according to claim 13, wherein the amount of Mg in the melt is increased if the nodularity is below a predetermined threshold value.

15. A computer program product comprising a program stored on a non-transitory computer readable medium for performing all the steps of claim 1 when the program product is run on a computer.

16. A computer system for implementing the method of claim 1 comprising a processor operable to run a computer program for performing all the steps of claim 1.

17. A method of analyzing an iron melt for producing compacted graphite iron, comprising the steps of
receiving thermal data from cooling of a cast melt comprising a predetermined amount of carbon, magnesium, balance iron and unavoidable impurities,
plotting a temperature of the cast melt against time such that a plotted time-temperature curve is generated,
predicting a nodularity of the cast melt by comparing the generated plotted curve to at least one reference curve, the reference curve representing a corresponding thermal analysis of another melt, a resulting nodularity of which is known, based on a difference between the curves,
wherein any of the curves is multiplied with a time factor such that a length of the curves expressed as t2 minus t1 becomes the same.

18. A method according to claim 17, wherein the comparison on which the nodularity is predicted is performed along each of the curves for a time interval t1–t2 corresponding to a temperature interval T1–T2, where T1 is in the range of TEstart–TEmin, where TEstart is the temperature of beginning formation of graphite in the melt and TEmin is a minimum temperature before start of eutectic recalescence in the melt, and T2 is in the range of Tsolidus–(Tsolidus–20° C.), and that other time intervals in the curves are excluded from the comparison.

* * * * *